United States Patent [19]

Ezaki et al.

[11] 4,027,014
[45] May 31, 1977

[54] ANTIBIOTIC BN-130 SUBSTANCES AND THE PRODUCTION THEREOF

[75] Inventors: Norio Ezaki, Yokohama; Shoichi Amano, Kawasaki; Shinji Miyado, Yokohama; Mitsugu Ito, Kawasaki; Chuhei Nojiri, Yokohoma; Takashi Tsuruoka, Kawasaki; Yujiro Yamada; Taro Niida, both of Yokohama, all of Japan

[73] Assignee: Meiji Seika Kaisha, Ltd., Tokyo, Japan

[22] Filed: Apr. 14, 1975

[21] Appl. No.: 567,867

[30] Foreign Application Priority Data

Apr. 17, 1974 Japan ................................ 49-42267

[52] U.S. Cl. ................................ 424/122; 195/80 R

[51] Int. Cl.$^2$ ............................................ A61K 35/74
[58] Field of Search ...................... 424/122; 195/80

[56] References Cited

UNITED STATES PATENTS 3,843,784   10/1974   Hamill et al. .................... 424/122

*Primary Examiner*—Jerome D. Goldberg
*Attorney, Agent, or Firm*—Larson, Taylor and Hinds

[57] ABSTRACT

A new antibiotic designated BN-130 substance is now provided, which has antibacterial activity against gram-negative and gram-positive bacteria as well as acid-fast bacteria. BN-130 substance is produced by cultivating a strain of *Pseudomanas stutzeri* under aerobic conditions.

6 Claims, 4 Drawing Figures

ANTIBIOTIC BN-130 SUBSTANCES AND THE PRODUCTION THEREOF This invention relates to a new and useful antibiotic substance designated as BN-130 substance which exhibits a high activity inhibitory to the growth of gram-positive and gram-negative bacteria as well as acid-fast bacteria. This invention further relates to a process for the production of this new antibiotic by cultivation of a strain of the genus Pseudomonas. This invention also relates to the recovery and purification of this new antibiotic substance and to its use for pharmaceutical purpose.

Many antibiotics which are useful for therapeutic purpose are known. In an attempt to obtain a further new and useful antibiotic which has a high antibacterial activity to various kinds of bacteria, we collected various soil samples, isolated microorganisms from such soil samples and investigated metabolism products which are produced by cultivation of the isolated microorganisms. We isolated a new microorganism from a soil sample collected in Nima-machi, Shimane-Prefecture, Japan, and we have designated this new microorganism as BN-130 strain. It has been confirmed that this BN-130 strain belongs to the genus Pseudomonas. We have now found that a new antibiotic substance having a high activity inhibitory to the growth of gram-positive and gram-negative bacteria as well as acid-fast bacteria is produced and accumulated in the culture broth of the BN-130 strain. We have now succeeded in isolating this new antibiotic substance from the culture broth and designated this antibiotic as BN-130 substance.

An object of this invention is to provide a new antibiotic substance which is useful as an antibacterial agent. Other object of this invention is to provide the BN-130 substance, either as a pure product or as a crude product. Further object of this invention is to provide a process for the production of the BN-130 substance by cultivation of BN-130 strain. Another objects of this invention will be clear from the following descriptions.

According to an aspect of this invention, there are provided as new compounds BN-130 substance having an antibacterial activity to gram-negative and gram-positive bacteria as well as acid-fast bacteria; said substance being a colorless or faintly yellow colored oil which has no definite melting point, becomes ice-like in the vicinity of 0° C and is in the state of oil in the vicinity of 40° C; said substance being of acidic nature and having carboxylic group; said substance being soluble in methanol, ethanol, n-butanol, acetone, ethyl acetate and methyl isobutyl ketone and slightly soluble in benzene and chloroform but insoluble in water; showing an optical rotation of $[\alpha]_D^{25}$ minus 19.2° in its 1% methanolic solution; being positive to potassium permanganate reaction and iodine reaction but negative to ninhydrin reaction, silver nitrate reaction, Sakaguchi reaction and ferric chloride reaction; giving an elemental analysis C 65.24%, H 8.79%, N 4.85% and O 21.12% (balance); showing a molecular weight of 520 as determined by the titration method and a molecular weight of 550 as calculated from the determination of the vapor pressure of the methyl ester of said substance; having an ultraviolet absorption spectra corresponding to those shown in FIG. 1 and an infrared absorption spectrum pelleted in potassium bromide corresponding to that shown in FIG. 2; and giving an $R_f$ value of 0.45 in thin layer chromatography on silica gel with ethyl acetatemethanol (20:1 by volume) and an $R_f$ value of 0.23 in the same thin layer chromatography on silica gel with chloroform-isopropanol (9:1 by volume) and a pharmaceutically acceptable salt of the BN-130 substance.

BN-130 substance may be converted into an alkali metal salt, for example, sodium salt and potassium salt, ammonium salt, and an alkaline earth metal salt such as calcium salt, magnesium salt, by neutralizing with an alkali metal hydroxide or an alkaline earth metal hydroxide.

BN-130 substance may be esterified by reacting with an alkanol of 1-4 carbon atoms such as methanol, ethanol, propanol in a conventional manner for esterification of a carboxylic acid. Methyl ester of BN-130 substance which is obtained by reacting the free acid form of BN-130 substance with methanol in the presence of a condensation catalyst such as concentrated sulfuric acid may further be acetylated by reacting with acetic anhydride. The acetylated methyl ester of BN-130 substance so obtained is in the form of a colorless or faintly yellow colored, crystalline powder.

Referring to the attached drawings.

1. Properties of BN-130 substance (the free acid form)

1. Appearance: Colorless or faintly yellow colored oil.

2. Elemental analysis: C 65.24%, H 8.79% N 4.85%, O 21.12% (balance)

It is found that BN-130 substance does not give the other elements than the carbon, hydrogen, nitrogen and oxygen upon its elemental analysis.

3. Molecular weight: BN-130 substance shows a molecular weight of 520 as determined by the titration method, but it shows a molecular weight of 550 as calculated from the determination of the vapor pressure of the methyl ester of BN-130 substance.

4. Melting point: No definite melting point is not shown. BN-130 substance becomes ice-like in the vicinity of 0° C when cooled, and it shows the state of oil in the vicinity of 40° C.

5. Specific optical rotation: $[\alpha]_D^{25} -19.2°$ (c=1 methanol)

Figure 1:
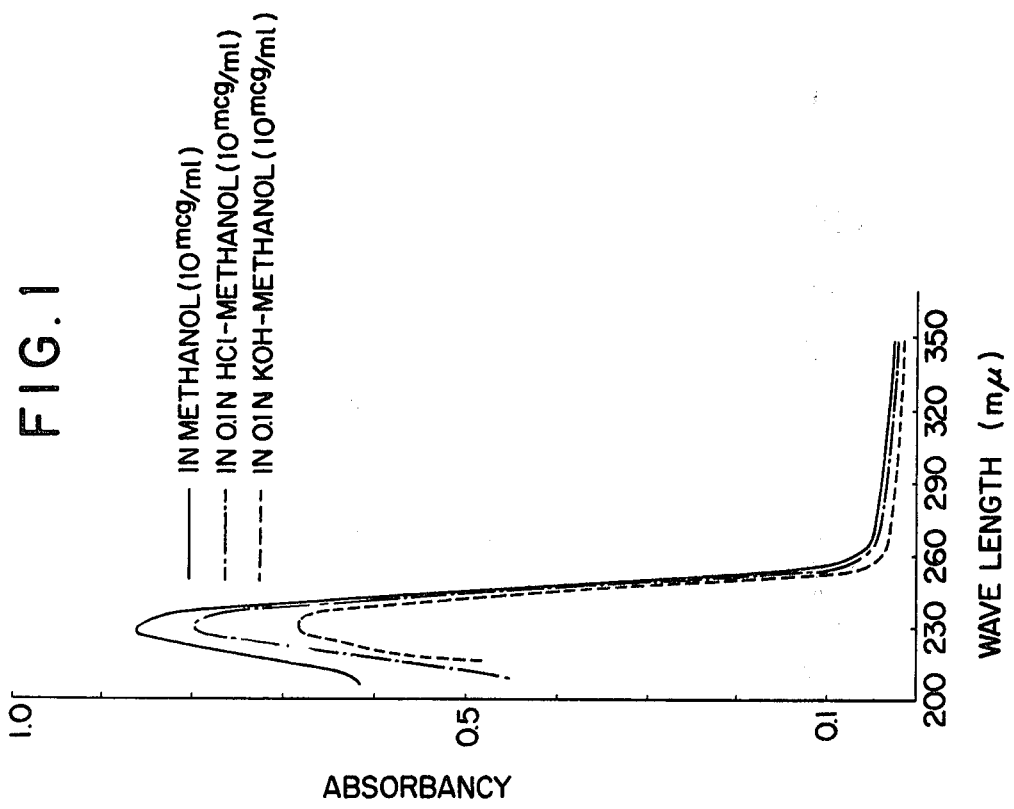
FIG. 1 shows curves of the ultraviolet absorption spectrum of a sample of BN-130 substance (the free acid form) dissolved in methanol, in 0.1N HCl-methanol and in 0.1N KOH-methanol, respectively.

6. Ultraviolet absorption spectrum:

The spectra of BN-130 substance in a solution of 10 mcg/ml of BN-130 substance in methanol, in a solution of 10 mcg/ml of BN-130 substance in 0.1N HCl-methanol and in a solution of 10 mcg/ml of BN-130 substance in 0.1N KOH-methanol are shown in FIG. 1. These spectra are characterized by absorption maxima at 227 m$\mu$ ($E_1^{1\%}{}_{cm}$ 860) in the methanol solution; at 227 m$\mu$ ($E_1^{1\%}{}_{cm}$ 800) in the 0.1N HCl-methanol solution and at 233 mμ ($E_1^{1\%}{}_{cm}$ 680) in the 0.1N KOH-methanol solution.

Figure 2:
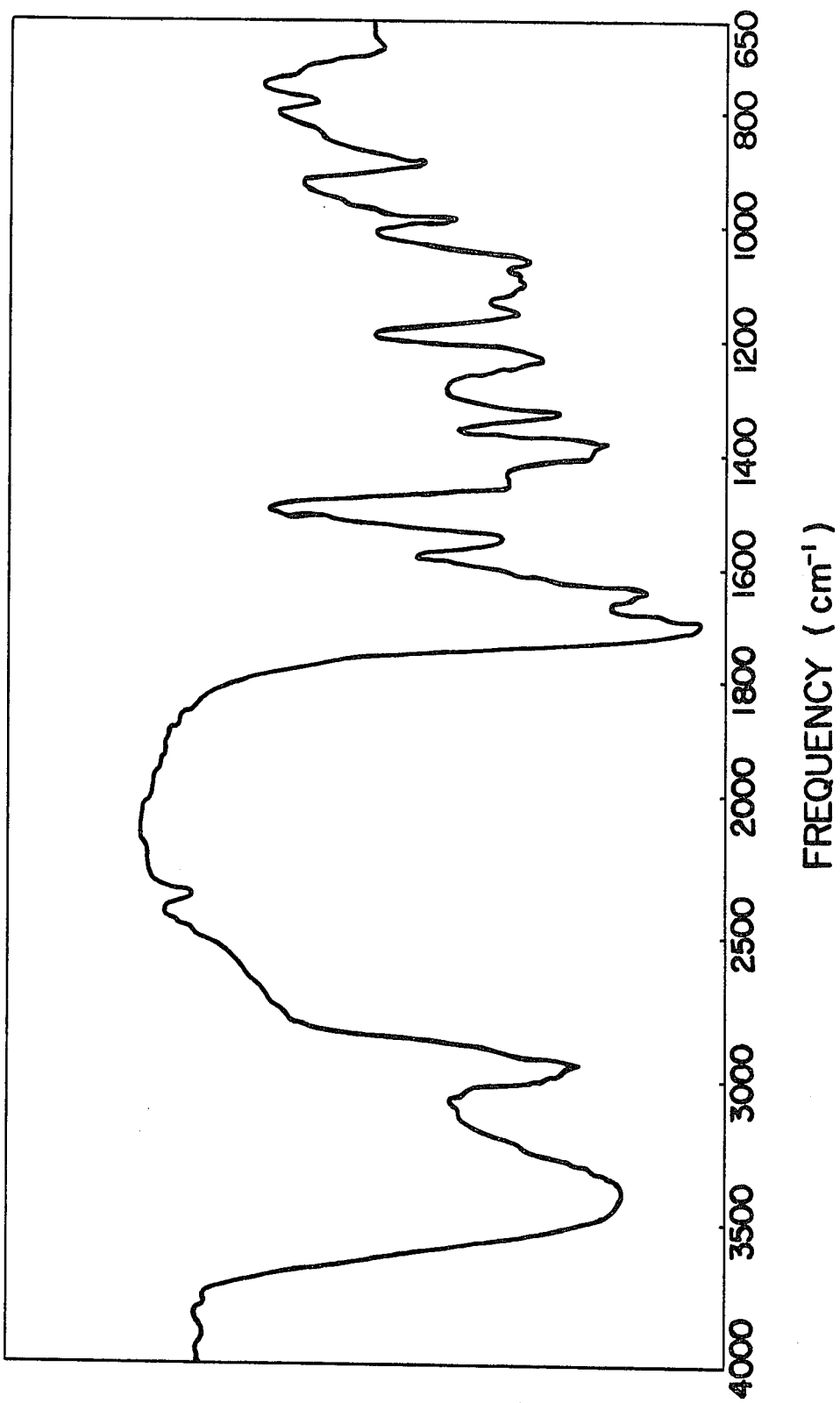
FIG. 2 shows a curve of the infrared absorption spectrum of a sample of BN-130 substance (the free acid form) pelleted in potassium bromide.

7. Infrared absorption spectrum: The spectrum of BN-130 substance pelleted in potassium bromide is shown in FIG. 2 and is characterized by absorption peaks at 3380, 2940, 1700, 1640, 1550, 1450, 1400, 1380, 1330, 1230, 1150, 1100, 1060, 990, 890 and 780).

8. Solubility in solvents: Readily soluble in methanol, ethanol, n-butanol, acetone, ethyl acetate and methyl isobutyl ketone; slightly soluble in benzene and chloroform; and insoluble in water.

9. Coloration reaction: Positive to potassium permanganate reaction and iodine reaction but negative to ninhydrin reaction, silver nitrate reaction, Sakaguchi reaction and ferric chloride reaction.

10. Filter paper electrophoresis: BN-130 substance does not move under acidic conditions (pH 1.9 at 3,000 volts, subjected to electrophoresis for 10 minutes) but it moves towards the anode by 1.8 cm under alkaline conditions (pH 8.1 at 300 volts, subjected to electrophoresis for 2 hours), revealing that BN-130 substance is an acidic substance.

11. $R_f$ value in silica gel thin layer chromatography: $R_f$ value is 0.45 when developed with ethyl acetate-methanol (20:1 by volume), and $R_f$ value is 0.23 when developed with chloroform-isopropanol (9:1 by volume) as the development solvent.

II. Properties of the acetylated methyl ester of BN-130 substance.

1. Appearance: Colorless or slightly yellow colored crystalline powder.

2. Elemental analysis: C 64.43%, H 8.40%, N 4.40%, O 22.77% (balance)

3. Molecular weight: The acetylated methyl ester of BN-130 substance has a molecular weight of 600 as determined by the vapor pressure method.

4. Melting point: 85°–87° C

5. Specific optical rotation: $[\alpha]_D^{25}$ −16.2° (c=1, methanol)

Figure 3:
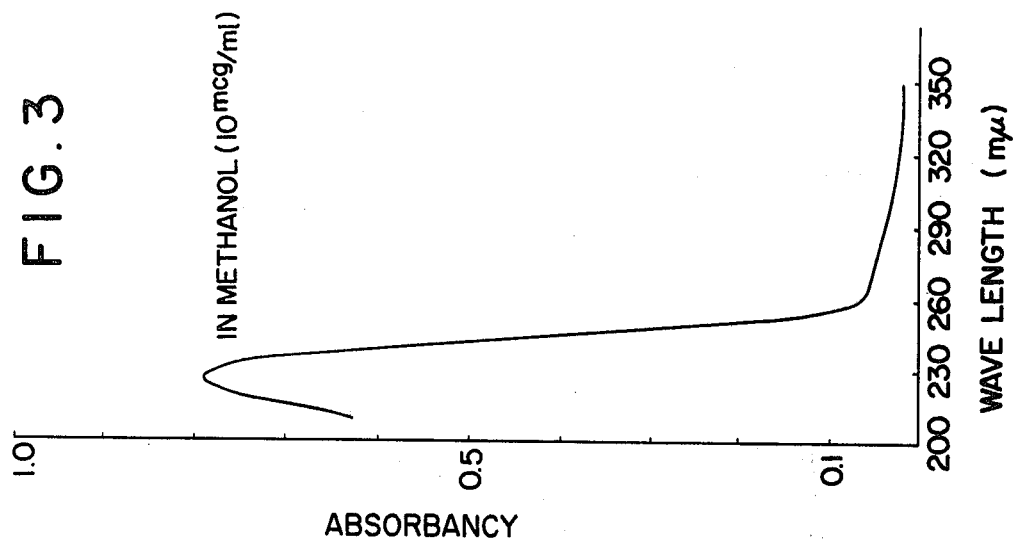
FIG. 3 shows a curve of the ultraviolet absorption spectrum of a sample of the acetylated methyl ester of BN-130 substance dissolved in methanol.

6. Ultraviolet absorption spectrum: The spectrum of the acetylated methyl ester of BN-130 substance in a solution of 10 mcg/ml of the acetylated methyl ester derivative in methanol is shown in FIG. 3 and is characterized by absorption mexima at 227 mμ ($E_1^{1\%}{}_{cm}$ 790).

Figure 4:
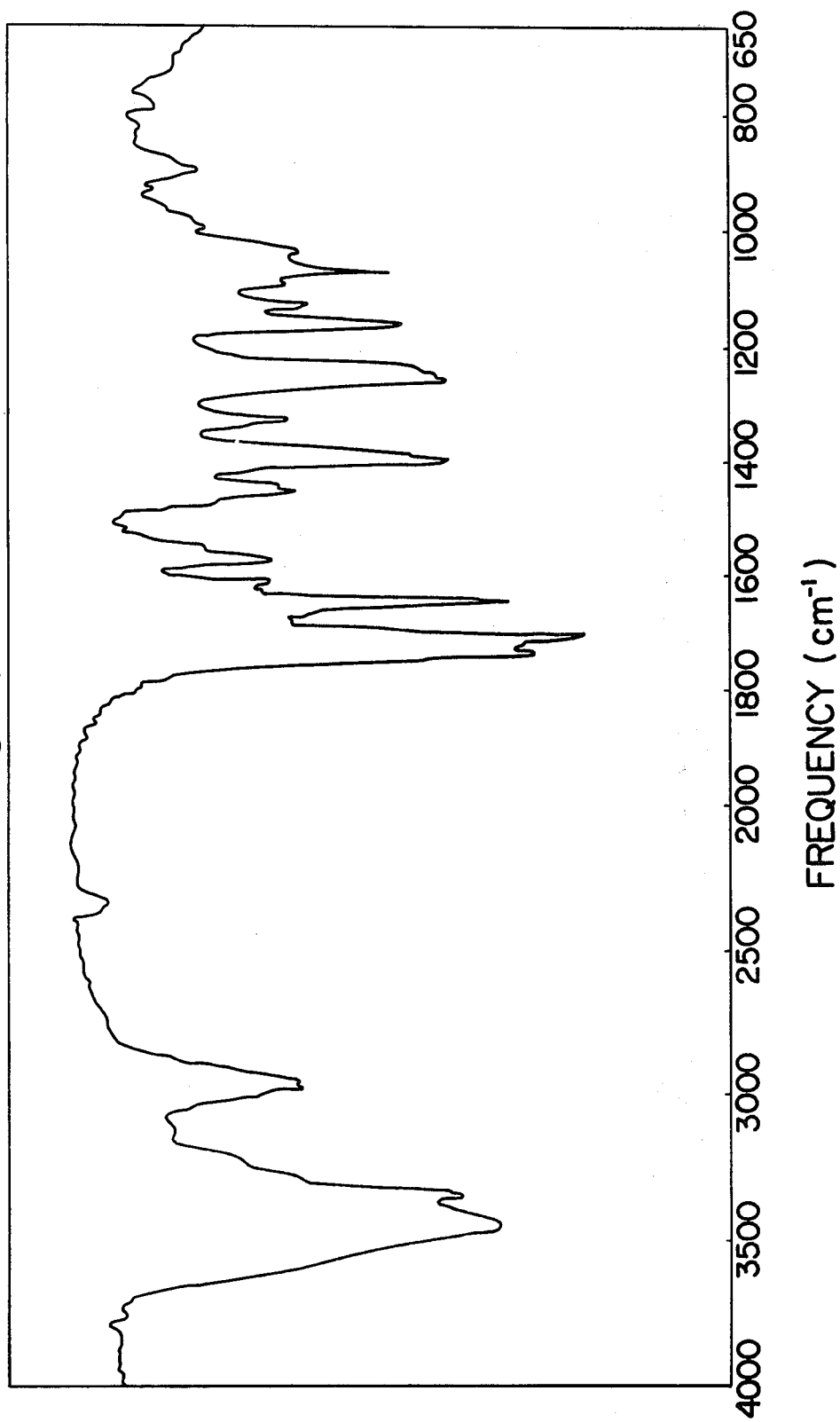
FIG. 4 shows a curve of the infrared absorption spectrum of a sample of the acetylated methyl ester of BN-130 substance pelleted in potassium bromide. Physical and chemical properties of BN-130 substance (the free acid form) and of the acetylated methyl ester of BN-130 substance are described below.

7. Infrared absorption spectrum: The spectrum of the acetylated methyl ester of BN-130 substance pelleted in potassium bromide is shown in FIG. 4 and is characterized by absorption peaks at 3450, 3340, 2980, 2940, 1730, 1700, 1640, 1610, 1570, 1450, 1400, 1330, 1260, 1250, 1160, 1130, 1090, 1070, 1040, 990, 890 and 790 cm$^{-1}$.

8. Solubility in solvent: Readily soluble in methanol, ethanol, n-butanol, acetone, ethyl acetate and methyl isobutyl ketone; soluble in chloroform, slightly soluble in benzene but insoluble in petroleum ether and water.

9. Coloration reaction: Positive to potassium permanganate reaction and iodine reaction, but negative to ninhydrin reaction, silver nitrate reaction, Sakaguchi reaction and ferric chloride reaction.

10. Filter paper electrophoresis: The acetylated methyl ester does not move from the original spot either under alkaline conditions (pH 8.1 at 300 volts, subjected to electrophoresis for 2 hours) or under acidic conditions (pH 5.1, at 300 volts, subjected to electrophoresis for 2 hours).

11. $R_f$ value in silica gel thin layer chromatography: $R_f$ value is 0.68 when developed with ethyl acetate-methanol (20:1 by volume), and $R_f$ value is 0.41 when developed with chloroform-isopropanol (9:1 by volume) as the development solvent.

The BN-130 substance of this invention has high antibacterial activity as will be clear from the antibacterial spectrum of this substance shown in Table 1 below. The minimum inhibitory concentrations (mcg/ml) of BN-130 substance to various bacteria have been determined on various incubation media indicated in Table 1 which were incubated at a temperature of 37° C for 16 hours.

Table 1

| Test organisms | Minimum Inhibitory concentration (mcg/ml) BN-130 | Incubation media |
|---|---|---|
| Bacillus subtilis ATCC 6633 | >100 | 1 |
| Sarcina lutea | >100 | 1 |
| Staphylococcus aureus 209P | 1.5 | 1 |
| Staphylococcus aureus 52–34 resistant to erythromycin-tetracycline | 0.025 | 1 |
| Escherichia coli | 3.1 | 1 |
| Pseudomonas aeruginosa | >100 | 1 |
| Klebsiella pneumonia | 12.5 | 1 |
| Proteus vulgaris | 0.3 | 1 |
| Mycobacterium smegmatis 607 | 6.25 | 2 |
| Candida albicans | >100 | 3 |

Notes: In the above Table,
(1) Medium 1 denotes bouillon medium; medium 2 glycerine-bouillon medium; and medium 3 glucose-peptone medium.
(2) The values of M.I.C. were determined according to a standard broth dilution method.

It has been observed that the sodium salt of BN-130 substance exhibits an antibacterial activity substantially as high as that of the free acid form of BN-130 substance.

The BN-130 substance of this invention exhibits a high antibacterial activity to various bacteria and particularly to Staphylococcus aureus as shown in the above table, and this new antibiotic has a low toxicity as shown by the fact that all mice could survive after a dose of 400 mg/kg of BN-130 substance (the free acid form) was intraperitoneally administered to the mice and also when doses of up to 1,000 mg/kg of BN-130 substance were orally administered to the mice for the purpose of estimate acute toxicity of BN-130 substance. Therefore, BN-130 substance of this invention is useful as an agent for treating therapeutically various infections caused by bacteria, and it is also useful for sterilization by surgical tool and materials accompanied by mechanical cleansing.

For the purpose of treating therapeutically the bacterial infections, the new BN-130 substance of this invention may be administered orally or parenterally, for example, by intraperitoneal, intravenous, subcutaneous or intramuscular injection. For the parenteral administration, the new substance of this invention may be used in conventional dosage forms, for example, in sterilized solution in a pharmaceutically acceptable organic solvent such as ethanol. A sterile aqueous solution of the sodium salt of BN-130 substance may be used for the parenteral administration. For oral administration, the new substance of this invention may be used also in conventional dosage forms known in the art, for example, in the form of powders, capsules, tablets, suppositories, ointment, syrups and the like, together with known pharmaceutically acceptable carrier. Suitable dosage of the new substance of this invention varies depending upon the nature of particular bacterial infection to be treated and may experimentally be determined by the skilled in the art in a known manner similarly to when a suitable dosage of known antibiotics such as streptomycin, kanamycins and others were determined for the treatment of various bacterial infections. It is added that the aforesaid acetylated methyl ester of BN-130 substance has substantially no antibacterial activity.

According to a further aspect of this invention, therefore, there is provided a pharmaceutical composition suitable for use in treating bacterial infections in a living animal, comprising a therapeutically effective amount of the BN-130 substance and/or a pharmaceutically acceptable salt of the BN-130 substance, in combination with a pharmaceutically acceptable carrier. According to another aspect of this invention, there is provided a process for treating therapeutically bacterial infections in living animals, which comprises administering a pharmaceutically effective amount of the BN-130 substance and/or a pharmaceutically acceptable salt of the BN-130 substance to an animal affected with bacterial infections.

As stated hereinbefore, BN-130 substance of this invention is produced and accumulated in a culture broth of a new microorganism designated as the BN-130 strain which belongs to the genus Pseudomonas. According to a fourth aspect of this invention, therefore, there is provided a process for the production of the BN-130 substance, which comprises cultivating a BN-130 substance-producing strain of the genus Pseudomonas in a suitable culture medium therefore containing assimilable carbon and nitrogen sources under aerobic conditions for a period of time sufficient to produce and accumulate the BN-130 substance in the culture medium, and recovering the BN-130 substance from the culture. For the production of BN-130 substance according to this invention, any strain of the genus Pseudomonas may be employed as long as this strain produces BN-130 substance. A suitable example of the BN-130 substance-producing strain of the genus Pseudomonas which may be employed in the process of this invention is the above-mentioned BN-130 strain of the genus Pseudomonas. This BN-130 strain was deposited on 17th Jan., 1974, in a Japanese authorized depository "Fermentation Research Institute, Agency of Industrial Science and Technology," Inage, Chiba-City, Japan, under deposit under FERM-P 2443. This BN-130 strain is deposited also in the American Type Culture Collection, Washington C.C., U.S.A., under ATCC number 31147.

Cultural and taxonomic characteristics of the BN-130 strain are described below.

I. Morphological Properties

Rod, 0.6 to 0.8 by 1.5 to 3.0 microns on nutrient agar. Motile with polar mono-trichous flagellum. Spore not formed Gram-negative.

II. Cultural Properties

1. Nutrient agar colonies (incubated at 28° C.): The colonies of freshly isolated strains are light brown in colour and of the rough form, wrinkled, dry and coherent. No diffusible pigments produced. In glucose media, this strain grows actively. The culture gives a putrescence odor.

2. Nutrient Broth (incubated at 28° C): Thin and flexible surface growth is observed.

3. Nutrient gelatin stab (incubated at 23° C): The medium is liquefied.

III. Physiological properties

1. Reduction of nitrate: Positive when incubated at 28° C for 3 days (The nitrate concentration in the order of 0.2% is suitable for the reduction of nitrate.

2. Denitrification: Positive when incubated at 28° C for 3 days (the nitrate concentration in the order of 0.2% is suitable for the denitrification).

3. Methyl-red test: Negative when incubated at 28° C for 3 or 5 days.

4. Voges-Proskauer test: Negative when incubated at 28° C for 3 or 5 days.

5. Production of indole: Negative when incubated 28° C for 3 or 5 days.

6. Production of hydrogen sulfide: Negative as detected by lead acetate paper method.

7. Hydrolysis of starch: Positive when incubated at 28° C for 3 days.

8. Production of pigment: Not observed on King medium.

9. Oxidase test: Positive when incubated at 28° C for 2 days.

10. Catalase test: Positive.

11. Temperatute suitable for growth: The BN-130 strain reproduces the cell at 20°–37° C but does neither reproduce the cell at 5° C nor at 42° C.

12. Oxidation-Fermentation test (according to Hugh-Leifson method): The BN-130 strain cannot grow under anaerobic conditions but produces acidic substances from glucose under aerobic conditions.

13. Utilization of carbon sources for growth: The strain can use glucose, maltose, starch or cellobiose as sole carbon source for growth, but cannot use galactose, L-arabinose, 2-ketogluconic acid, glycolate, propylene glycol, p-hydroxybenzoic acid, $\beta$-alanine or L-histidine.

14. Susceptibility to antibiotics: Susceptible to: Tetracycline, nalidixic acid, colistin and polymixin. Susceptible to a medium degree to: Chloramphenicol, streptomycin and kanamycin. Resistant to: Penicillin, aminobenzylpenicillin, and cephaloridine.

Comparing the BN-130 strain having the abovementioned microbiological properties with such known strains which have similar properties, the following conclusion has been reached:

1. The BN-130 strain is estimated to belong to the genus Pseudomonas in view of that it is a gram-negative rods and is morphologically characterized by that it does not produce spore but moves with the polar flagellum, and in view of that it cannot make any energy metabolism of fermentation type.

2. The BN-130 strain is considered to belong to the Pseudomonas stutzeri group in view of that it forms wrinkled colonies and that it causes denitrification reaction of a nitrate compound and hydrolyses starch.

3. It seems most reasonable that the BN-130 strain is judged to belong to the species Pseudomonas stutzeri, because the BN-130 strain is similar in many points to a known ideal phenotype of Psuedomonas stutzeri which have been defined with reference to its polar mono-trichous flagellum, its denitrifying ability and its utilization of 11 carbon compounds by Stanier et al's classification of the genus Pseudomonas (the "Journal of General Microbiology" Vol. 43, page 159 (1966) and by Palleroni et al's classification of Pseudomonas stutzeri group (the "Journal of General Microbiology" Vol. 60, page 215 (1970), though the BN-130 strain is a little differentiated from the known ideal phenotype of P. stutzeri in respect to the utilization of cellobiose, propylene glycol and glycolate; and because apparently it is rather unreasonable to decide that the BN-130 strain would belong to any other species than P. stutzeri.

4. The BN-130 strain has such a susceptibility to antibiotics which well coincides with that of *P. stutzeri* as reported by Yabu-uchi et al (the "Media Circle" Vol. 16, page 6 (1971).

From the above comparison, we have confirmed that the BN-130 strain is a new strain of the known species *Pseudomonas stutzeri* and should be differentiated from the known strains of the latter. Accordingly, we have designated the BN-130 strain as *Pseudomonas stutzeri* BN-130.

According to an embodiment of the fourth aspect process of this invention, there is provided a process for the production of the BN-130 substance, which comprises cultivating a BN-130 substance-producing strain of *Psuedomonas stutzeri* or particularly *Pseudomonas stutzeri* BN-130 identified as FERM-P 2443 in a suitable culture medium therefore containing assimilable carbon and nitrogen sources under aerobic conditions for a period of time sufficient to produce and accumulate the BN-130 substance in the culture medium, and recovering the BN-130 substance from the culture.

For the production of BN-130 substance, a BN-130 substance-producing strain of the genus *Pseudomonas*, particularly the BN-130 strain (identified as FERM-P 2443) may be cultivated in a known manner under aerobic conditions in a suitable culture medium containing such carbon and nitrogen sources which are utilisable as the nutrients by usual microorganisms for the fermentation. For instance, glucose, starch, starch syrup, molasses and the like are useful as the carbon source. Further, soybean meal, soluble vegetable protein, corn steep liquor, peptone, meat extract and other suitable organic nitrogeneous compounds as well as such inorganic nitrogeneous compounds such as ammonium sulfate, ammonium chloride, sodium nitrate and the like are useful as the nitrogen source. If required, inorganic salts such as magnesium sulfate and calcium carbonate, etc., may be added to the culture medium. Vitamins and/or known anti-foaming surfactants may be incorporated into the culture medium, if necessary. As the procedure of cultivating the BN-130 strain, liquid cultivation method may suitably be employed. Shake-cultivation method and particularly liquid cultivation method under submerged aerobic conditions are most preferred similarly to the general process of producing known antibiotics. The cultivation of the BN-130 strain may suitably be carried out at a temperature in a range of 25° to 35° C and for a period of time in the range of 40 to 70 hours. The BN-130 substance is produced and accumulated mainly in the liquid phase of the culture broth.

For assay of the BN-130 substance, the following method may be employed: The assaying basal culture medium comprising peptone 1.0%, meat ext. 0.5%, NaCl 0.25%, Agar 2% (commercially available under a trade name "Penassay Agar," a product sold by Kyo-ei Seiyaku Co., Japan) is employed and the known species *Staphylococcus aureus* 209P is used as the assaying microorganism. In this assaying method, at a concentration of 5 mcg/ml to 1,000 mcg/ml of BN-130 substance (an authentic sample), the relation between the logarithm of the concentration and the diameter of the inhibition zone can be plotted linearly, giving the inhibition zone of 20 to 36 mm in diameter (as determined by the paper disc method).

The BN-130 substance as produced by the cultivation of the BN-130 strain is mainly present in the liquid phase of the culture broth and may be recovered from the culture by utilizing the aforesaid physical and chemical properties of BN-130 substance. The following procedure is efficient to recover BN-130 substance from the culture. Thus, the culture broth containing the active BN-130 substance is freed from the solid contents by filtration or centrifugation, and the resulting broth filtrate is made acidic by addition of hydrochloric acid or sulfuric acid. The acidified broth filtrate is extracted with a water-immiscible organic solvent such as ethyl acetate, butyl acetate, n-butanol or methyl isobutyl ketone, etc., and the organic extract is then concentrated under a reduced pressure, giving a crude produce of BN-130 substance. Alternatively, the culture broth is immediately made acidic by addition of hydrochloric acid or sulfuric acid to deposit a precipitate comprising the desired active BN-130 substance. The precipitate is removed by filtration and then extracted with an organic solvent such as acetone or methanol, etc., and the resulting extract is concentrated under reduced pressure to give a crude product of BN-130 substance. This crude product may further be purified by subjecting to a chromatographic process on silica gel or Sephadex LH-20 (a product of Pharmacia Co., Sweden), or active carbon and/or to a counter-current process with ethyl acetate and benzene, so that a pure product of BN-130 substance is afforded in the form of a colorless oil. By testing this colorless oil product in silica gel thin layer chromatography with various solvent systems, it was confirmed that the colorless oil product gave a single spot when developed with any of the solvent systems, revealing that said colorless oil should be the pure, authentic product of BN-130 substance.

To differentiate clearly BN-130 substance of this invention from known antibiotics which are produced by various *Pseudomonas* species, we have compared antibacterial activity and chemical properties of BN-130 substance with those of such known antibiotics. As a result, we have found that pseudomonic acid and its related compounds (see Japanese patent application pre-publication No. 8992/73) are similar to BN-130 substance of this invention. Nonetheless, it has been identified that pseudomonic acid and its related compounds do not contain the nitrogen as the constituent elements of these compounds and hence are evidently different from BN-130 substance which essentially contains the nitrogen as the constituent elements thereof. It has further been found that BN-130 substance of this invention coincides with none of the known antibiotics which are produced by bacteria and by actinomycetes. In consequence, we have concluded that BN-130 substance is a new antibiotic.

The present invention is now illustrated with reference to the following Examples to which the present invention is not limited.

EXAMPLE 1

20 Sakaguchi flasks of 500 ml capacity each containing 100 portion of a liquid culture medium comprising 2% glucose and 2% powdered bouillon were sealed with cotton plug, and the content of each flask was then sterilized by heating at 120° C for 10 minutes under pressure. To the sterilized culture medium in each flask was then inoculated a loopful amount of a slant culture of *Pseudomonas stutzeri* BN-130 (identified as FERM-P 2443). The inoculated medium was shake-cultivated at 32° C for 3 days to give 1.8 l of a culture broth containing 50 mcg/ml of BN-130 substance.

The culture broth was sterilized by heating at 100° C for 10 minutes and then adjusted to pH 2 by addition of hydrochloric acid. The acidified broth was extracted with 500 ml of ethyl acetate, and the ethyl acetate extract was concentrated under a reduced pressure. The concentrated solution so obtained was passed through a column of 80 ml of silica gel which had been impregnated with ethyl acetate. The column was then eluted with ethyl acetate, and the eluate was collected in 10 ml fractions. The active fraction Nos. 12 to 23 were combined together and concentrated to dryness under reduced pressure to obtain 80 mg of a yellow colored oil. This oil (80 mg) was taken up into 1 ml of ethyl acetate, and the resulting solution was passed through a column of 50 ml of "Sephadex LH-20" (a commercially available gel-filtration agent comprising dextran sold by Pharmacia Co., Sweden) which had been impregnated and swollen with ethyl acetate. The column was then eluted with ethyl acetate, and the eluate was collected in 7 ml fractions. The active fraction Nos. 13 to 19 are combined together and concentrated to dryness under reduced pressure, affording 38 mg of BN-130 substance (the free acid form) as a colorless oil. $[\alpha]_D^{25}$ −19.2° (c=1, methanol).

EXAMPLE 2

A culture medium (15 l) containing 0.5% glucose, 2% soluble starch, 1% peptone, 0.7% meat extract, 0.1% $MgSO_4.7H_2O$ and 0.03% of anti-foaming silicone oil which was placed in a 30 l tank-fermentor was sterilized by heating at 120° C for 10 minutes and then cooled to ambient temperature. To this sterilized medium was inoculated a seed culture (200 ml) of the BN-130 strain which had been incubated for 2 days in 2 Sakaguchi flasks containing the culture medium of the same composition as stated above. The inoculated medium was cultivated at 30° C for 2 days under agitation and aeration (at an agitator speed of 240 r.p.m., and at an aeration rate of 15 l/min) to give 13 l of the culture broth containing 100 mcg/ml of BN-130 substance.

The culture broth was sterilized by heating at 100° C for 10 minutes and then freed from the solid matter by filtration. The broth filtrate so obtained was adjusted to pH 1.5 by addition of hydrochloric acid and then admixed with 5 l of methyl isobutyl ketone with stirring to extract the active BN-130 substance therefrom. The methyl isobutyl ketone layer (the extract) was separated from the aqueous layer and then agitated together with 5 l of an alkaline water which had been adjusted to pH 10 by addition of aqueous sodium hydroxide, so that the active BN-130 substance was transferred into the aqueous layer. The aqueous layer was separated from the organic solvent layer, then adjusted to pH 1.5 by addition of hydrochloric acid and subsequently extracted again with 2 l of methyl isobutyl ketone under agitation. The methyl isobutyl ketone layer (the extract) so obtained was separated from the aqueous layer and then passed through a column of 50 g of chromatographing active carbon granules which had been impregnated with methyl isobutyl ketone. The carbon column was washed with methyl isobutyl ketone and then with acetone and subsequently eluted with 0.1N ammonia-70% aqueous n-propanol (that is, a mixture of 70% by volume of n-propanol and 30% by volume of water containing 0.1N ammonia) to desorb the active BN-130 substance from the carbon. The eluate was collected in 100 ml fractions, and the active fraction Nos. 2 to 6 were combined together to a total volume of 500 ml and then concentrated to a volume of 50 ml under reduced pressure. The concentrated solution was adjusted to pH 1.5 by addition of hydrochloric acid and then extracted with 30 ml of ethyl acetate to isolate the active BN-130 substance. The ethyl acetate phase (the resulting extract) was concentrated to dryness under reduced pressure, giving 800 mg of a partially purified product of BN-130 substance as a faintly yellow oil. This oil was dissolved in 3 ml of a mixed solvent consisting of benzene-acetone (5:2 by volume), and the solution so obtained was passed through a column of 80 ml of silica gel which had been impregnated with a further amount of the same mixed solvent. The silica gel column was washed with the same mixed solvent and then subjected to gradient-chromatography with increasing stepwise the concentration of acetone in the mixed solvent used as the developing solvent. The eluate was collected in 15 ml fractions. The active fraction Nos. 55 to 62 containing BN-130 substance were combined together and concentrated to dryness under reduced pressure to yield 320 mg of a pure BN-130 substance as a colorless oil. $[\alpha]_D^{25}$ −19.2° (c=1, methanol).

EXAMPLE 3

A culture medium (300 l) comprising 0.5% glucose, 2% soluble starch, 2% defatted soybean meal, 1% corn steep liquor, 0.1% $MgSO_4.7H_2O$ and 0.01% antifoaming silicone oil which was placed in a 570 l tankfermentor was sterilized by heating at 120° C for 30 minutes and then cooled to ambient temperature. To this sterilized medium was inoculated such a seed culture (15 l) of the BN-130 strain which had been obtained by preliminarily incubating for 1 day a stock culture of the BN-130 strain in an amount of the same culture medium as employed in Example 2. The inoculated medium was cultivated at 28° C for 2 days under aeration and agitation (at an aeration rate of 300 l/min and at an agitator speed of 180 r.p.m.) to give 280 l of a very viscous culture broth which contained BN-130 substance at a potency of 150 mcg/ml.

The culture broth was sterilized by heating at 100° C for 10 minutes, followed by cooling and addition of 90 l of water. The diluted culture broth was then adjusted to pH 1.5 by addition of hydrochloric acid and admixed with 30 kg of filter-aid under stirring. The admixture was filtered to obtain 70 kg of a moistened filter cake. This cake was mixed with 60 l of methanol and the mixture was adjusted to pH 7 by addition of aqueous sodium hydroxide. The mixture was agitated for 2 hours so that the active substance was extracted into the methanol layer. The mixture was filtered to give a first methanolic extract as the filtrate. The filter cake so obtained was again admixed with 60 l of methanol under stirring, and the admixture was adjusted to pH 7 by addition of sodium hydroxide and agitated for 2 hours. The admixture was subsequently filtered to give a second methanolic extract as the filtrate. The combined first and second methanolic extracts were concentrated to a volume of 1.5 l by evaporation of the solvent under reduced pressure. The concentrated solution so obtained was adjusted to pH 1.5 by addition of hydrochloric acid and extracted with 1 l of methyl isobutyl ketone to isolate the BN-130 substance. The methyl isobutyl ketone layer was separated from the methanol layer and then extracted with two 500 ml portions of water which had been adjusted to alkaline pH 10 by addition of sodium hydroxide, so that the BN-130 substance was transferred into the aqueous layers. The combined aqueous extracts were adjusted to pH 1.5 by addition of hydrochloric acid and then again extracted with 1 l of methyl isobutyl ketone. The resulting extract in methyl isobutyl ketone was concentrated to dryness under reduced pressure to give 120 g of a yellowish brown colored oil. This oil was taken up into 100 ml of ethyl acetate, and the solution in ethyl acetate was passed through a column of 1.5 l of silica gel which had been impregnated with ethyl acetate. The silica gel column was developed with ethyl acetate, and the effluent from the column was collected in 500 ml fractions. The active fraction Nos. 3 to 10 containing the desired BN-130 substance were combined together and concentrated to dryness under reduced pressure to give 40 g of a yellow colored oil. This oil was taken up into 50 ml of ethyl acetate and the resulting solution was passed through a column of 1 l of "Sephadex LH-20" which had been impregnated with ethyl acetate. The column was developed with ethyl acetate, and the effluent from the column was collected in 50 ml fractions. The active fraction Nos. 35 to 62 containing the desired antibiotic were combined together and concentrated under reduced pressure, affording 13 g of the free acid form of BN-130 substance as a colorless oil. $[\alpha]_D^{25}$ −19.2° (c=1, methanol).

EXAMPLE 4

The BN-130 substance (100 mg) (the free acid form) was dissolved in 5 ml of methanol, and to the resulting solution was added a solution of diazomethane ($CH_2N_2$) in ethyl ether. The mixture was allowed to stand for 30 minutes under ice-cooling and then concentrated under reduced pressure, leaving 93 mg of an oil comprising the methyl ester of BN-130 substance. This oil (90 mg) was dissolved in a mixture of 3 ml of pyridine and 1.5 ml of acetic anhydride, and the resulting solution was allowed to stand for 3 days at 5° C under ice-cooling. The solution was then concentrated to a volume of about one-fourth of the original volume and then admixed with ice pieces. The precipitate deposited was collected by filtration and then dried over anhydrous magnesium sulfate to yield 110 mg of the acetylated methyl ester of BN-130 substance as a crystalline powder. mp. 85°–87° C.

What we claim is:

1. BN-130 substance having an antibacterial activity to gram-negative and gram-positive bacteria as well as acid-fast bacteria; said substance being a colorless or faintly yellow colored oil which has no definite melting point, becomes ice-like in the vicinity of 0° C and is in the state of oil in the vicinity of 40° C; said substance being of acidic nature and having carboxylic group; said substance being soluble in methanol, ethanol, n-butanol, acetone, ethyl acetate and methyl isobutyl ketone and slightly soluble in benzene and chloroform but insoluble in water; showing an optical rotation of $[\alpha]_D^{25}$ minus 19.2° in its 1% methanolic solution; being positive to potassium permanganate reaction and iodine reaction but negative to ninhydrin reaction, silver nitrate reaction, Sakaguchi reaction and ferric chloride reaction; giving an elemental analysis C 65.24%, H 8.79%, N 4.85% and O 21.12% (balance); showing a molecular weight of 520 as determined by the titration method and a molecular weight of 550 as calculated from the determination of the vapor pressure of methyl ester of said substance; having ultraviolet absorption spectra corresponding to those shown in FIG. 1 and an infrared absorption spectrum pelleted in potassium bromide corresponding to that shown in FIG. 2; and giving an $R_f$ value of 0.45 in thin layer chromatography on silica gel with ethyl acetate-methanol (20:1 by volume) and an $R_f$ value of 0.23 in the same thin layer chromatography on silica gel with chloroformisopropanol (9:1 by volume), or a pharmaceutically acceptable salt of the BN-130 substance.

2. Sodium salt of the BN-130 substance according to claim 1.

3. A process for the production of the BN-130 substance according to claim 1, which comprises cultivating the microorganism Pseudomonas stutzeri BN-130 identified as ATCC 31147 in a suitable culture medium containing assimilable carbon and nitrogen sources under aerobic conditions for a period of time sufficient to produce and accumulate the BN-130 substance in the culture medium, and recovering the BN-130 substance from the culture.

4. A process according to claim 3 in which Pseudomonas stutzeri BN-130 is cultivated at a temperature of 25°–35° C for a time of 40 to 70 hours.

5. An antibacterial pharmaceutical composition suitable for treating bacterial infections in a living animal, comprising an antibacterially effective amount of the BN-130 substance or a pharmaceutically acceptable salt of the BN-130 substance, in combination with a pharmaceutically acceptable carrier.

6. A process for treating therapeutically bacterial infections in living animals, which comprises administration an antibacterially effective amount of the BN-130 substance or a pharmaceutically acceptable salt of the BN-130 substance to an animal effected with bacterial infections.

* * * * *